United States Patent [19]

Konomi

[11] Patent Number: 4,505,583

[45] Date of Patent: Mar. 19, 1985

[54] SPECTROSCOPIC ANALYZER SYSTEM FOR EXAMINING INTRAVITAL TISSUE

[76] Inventor: Masaaki Konomi, 1-11-203, Sakurajosui 4-chome, Setagaya-ku, Tokyo, Japan

[21] Appl. No.: 363,855

[22] Filed: Mar. 31, 1982

[30] Foreign Application Priority Data

Apr. 10, 1981 [JP] Japan ................................. 56-53150
Jul. 2, 1981 [JP] Japan ................................. 56-102289

[51] Int. Cl.³ ...................... G01N 21/27; G01N 21/64
[52] U.S. Cl. .................................... 356/73; 356/417; 356/418; 356/419
[58] Field of Search .............. 356/407, 414, 416, 418, 356/320, 41, 73, 417, 419

[56] References Cited

U.S. PATENT DOCUMENTS

| | | | |
|---|---|---|---|
| 3,825,342 | 7/1974 | Lubbers et al. | 356/41 |
| 3,963,351 | 6/1976 | Chance et al. | 356/418 X |
| 4,180,327 | 12/1979 | Maeda et al. | 356/320 |
| 4,300,689 | 11/1981 | Franklin et al. | 356/407 |
| 4,340,307 | 7/1982 | Diamond et al. | 356/320 |

*Primary Examiner*—F. L. Evans
*Attorney, Agent, or Firm*—Warren B. Kice

[57] ABSTRACT

In a spectroscopic analyzer, light emitted from a light source is spectroscopically divided into a series of light rays of different wavelength by means of plural sets of interference filter for two-wavelength photometry adapted to intermittently and successively intercepting light from the light source or to be scanned by the light through a rotatable slit. An object under test is irradiated sequentially by the series of light rays transmitted through an optical fiber bundle. Reflected light rays carrying informations of the object are sequentially applied to photoelectric converter. Electric signals thus produced are digitized and arithmetically processed for obtaining a plurality of data corresponding to the plural sets of the interference filters.

8 Claims, 23 Drawing Figures

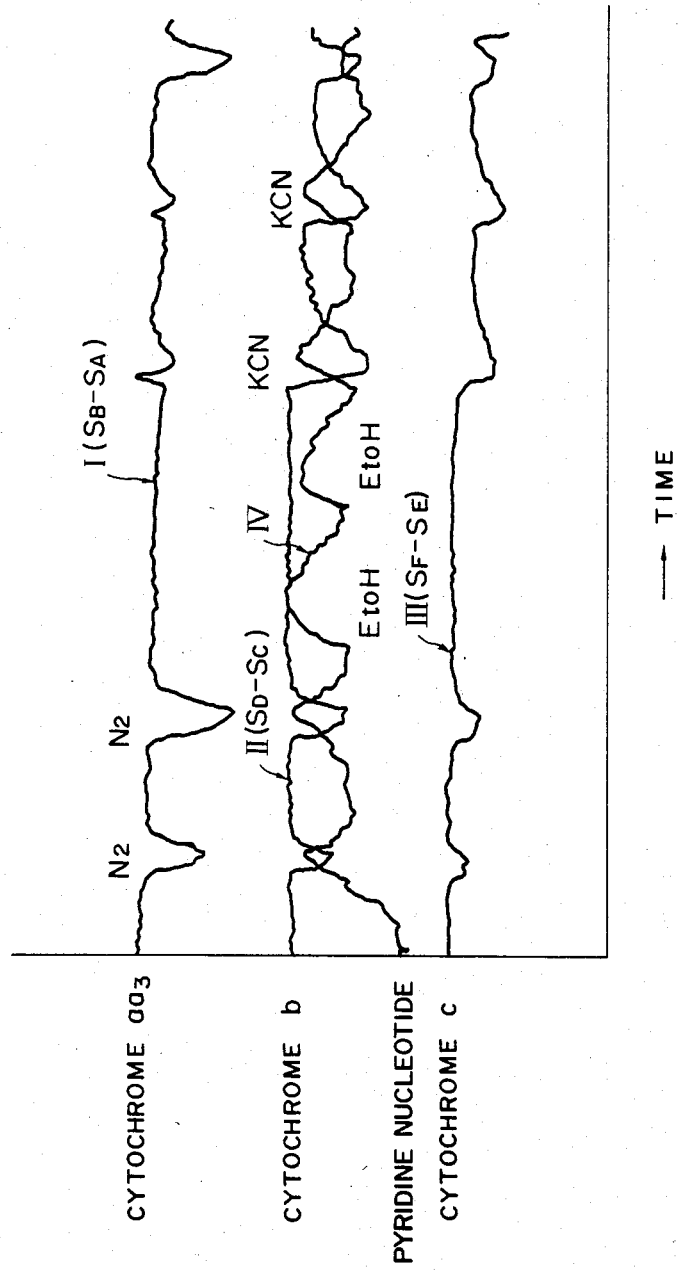

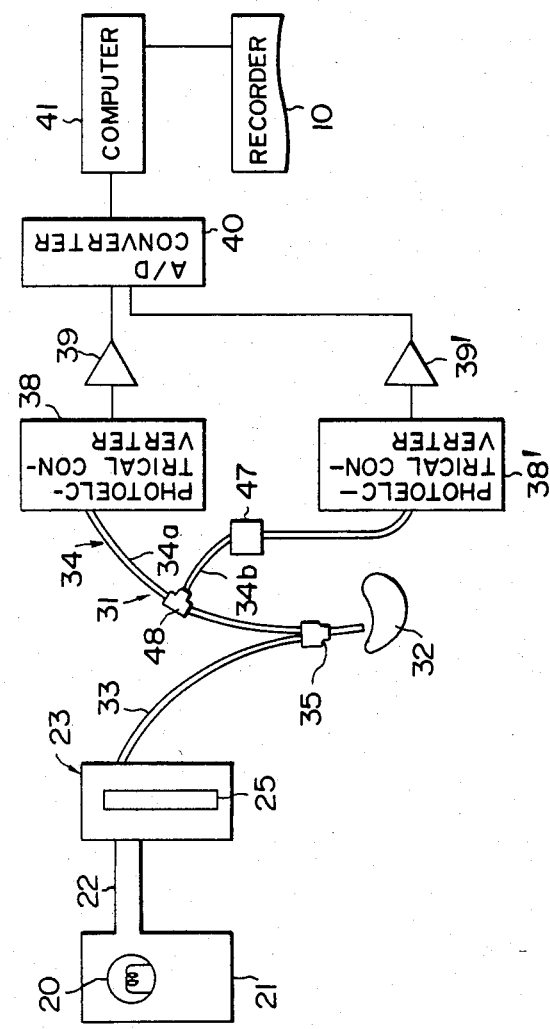

SPECTROSCOPIC ANALYZER SYSTEM FOR EXAMINING INTRAVITAL TISSUE

BACKGROUND OF THE INVENTION

The present invention relates generally to a spectroscopic analyzer system for analytically examining objects such as intravital tissues and the like of animals and plants with the aid of spectroscopic technique. In particular, the invention concerns a spectroscopic analyzer system for spectroscopically analyzing influences of oxygen concentration, metabolism of medicines, ischemia and the like to intravital objects such as tissues or organs of circulatory systems.

It is well known that intravital pigments of oxidation/reduction type such as, for example, cytochromes carried by mitochondoria in cells of respiratory systems exhibit absorption spectra which are remarkably different between oxidation and reduction types of pigments or cytochromes. By making use of this fact, it is possible to obtain biological or biogenical informations on the cell base through spectroscopical or photometrical detection and quantitative analyzation.

Heretofore, a so-called two-wavelength photometry has been adopted for obtaining the biological or biogenical informations of the type mentioned above. According to the principle of the two-wavelength photometry, measurement is made as to difference in absorption of an object under test between a maximal absorption wavelength (i.e. the wavelength at which difference in absorption between oxidation and reduction types of pigments in concern makes appearance most significantly) and a reference wavelength (i.e. the wavelength which approximates closely to the maximal absorption wavelength and at which difference in absorption is scarcely observed between the oxidation and reduction types). In the two-wavelength photometry, influence ascribable to turbidity of a specimen can be cancelled out because of its substantial equivalency at both wavelengths. Further, by selecting the wavelengths so as to be scarcely influenced by oxidation and/or reduction of other pigments, evaluation of pigment in concern can be effected with a high accuracy.

A typical example of hitherto known spectroscopic analyzer system which is operative based on the principle of the two-wavelength photometry mentioned above is schematically shown in FIG. 1. This system comprises a light source 1 of a predetermined range of wavelengths, a first monochromator 3 for deriving from the light source 1 light ray of a wavelength $\lambda_1$ at which the maximal absorption by a specimen 2 under test occurs (this wavelength is referred to as the maximal absorption wavelength), a second monochromator 4 for deriving the reference wavelength $\lambda_2$, a swingably vibrated mirror 5 for projecting alternately the two light beams of the different wavelength $\lambda_1$ and $\lambda_2$ to the specimen 2, a photoelectric converter element 6 for converting the light beams transmitted through the specimen 2 into corresponding electric signals, a chopper circuit 7 for separating the output signal from the photoelectric converter element 6 into signal components attributable to the wavelengths $\lambda_1$ and $\lambda_2$, respectively, signal conditioning circuits 8a and 8b for amplifying and standardizing output signals from the chopper circuit 7, a differential amplififer 9 for detecting difference between the output signals from the conditioning circuits 8a and 8b, and a recorder 10 for recording data on the basis of the output signal S from the differential amplifier 9 as a function of time.

Circuit configuration of the signal conditioning circuits 8a and 8b is schematically illustrated in FIG. 2. These circuits 8a and 8b comprise, respectively, variable gain amplifiers 11a and 11b for amplifying the incoming signals $S\lambda_1$ and $S\lambda_2$ originated, respectively, from the wavelengths $\lambda_1$ and $\lambda_2$ to an appropriate level, integrators 12a and 12b for integrating the output signals $S\lambda_1'$ and $S\lambda_2'$ produced from the variable gain amplifiers 11a and 11b for the purpose of removing noise and increasing sensitivity, and sample/hold circuits 13a and 13b for holding the outputs of the integrators 12a and 12b for a predetermined time. In this connection, it will be noted that the hold time $T_1$ of the sample and hold circuit 13a provided in the signal conditioning circuit 8a is different from the hold time $T_2$ of the sample and hold circuit 13b belonging to the signal conditioning circuit 8b, as is graphically illustrated in FIG. 3. This is because the output signals from the signal conditioning circuits 8a and 8b have to be simultaneously applied to the differential amplifier 9.

The hitherto known spectroscopic analyzer system described above however suffers from various and serious drawbacks. First, because a specific component of the specimen 2 in concern requires for the evaluation or identification thereof two light beams of different wavelengths $\lambda_1$ and $\lambda_2$, two monochromators 3 and 4 are indispensably required, involving inexpensiveness in respect of hardwares. Besides, every time when use of other wavelengths becomes necessary for identifying other components, interference filters (not shown) inserted in the monochromators 3 and 4 have to be correspondingly replaced by other ones, which requires not only troublesome procedures but renders it impossible to carry out identification of plural components in a continuous manner, involving inefficiency in operation. Further, the specimen 2 can be prepared only through a series of cumbersome procedures such as smashing, differential centrifugation, extraction, purification and containment in a cuvette. The specimen which requires such troublesome preparation can usually provide a single kind of data. For obtaining a number of desired data, the specimen must be prepared in consideration of various particular conditions, thus involving delicate and time consuming procedure as well as high expenditure. Further, difficulty will be encountered in management of stock materials for preparing such specimens. Moreover, the swingable mirror 5 for irradiating the specimen alternately with two light beams of different wavelengths gives rise to an instability in the optical path, providing a cause for generation of noise, to another disadvantage. Besides, use of the integrators 12a and 12b in the signal processing circuits 8a and 8b will integrate also the noise components, which means that the result of measurement is relatively poor in reliability and accuracy. Further, due to analog type configuration of the signal processing circuits 8a and 8b, a desired high speed operation can not be accomplished. Thus, the system on the whole is lacking in reliability and speedy operation.

SUMMARY OF THE INVENTION

It is accordingly an object of the present invention to provide a spectroscopic analyzer system which are immune to various disadvantages of the prior art described above.

Another object of the present invention is to provide a spectroscopic analyzer system which allows various kinds of data to be concurrently available from a single object under test on a time series base through a single spectroscopic process.

Still another object of the invention is to provide a spectroscopic analyzer system which allows identification or quantitative estimation of substances in concern to be carried out with a high accuracy at a high speed.

A further object of the invention is to provide a spectroscopic analyzer system which is capable of performing spectroscopic analyses of intravital tissues, organs and the like of living animals and plants in situ without necessity of preparing specific specimens.

According to an aspect of the invention, there is provided a spectroscopic analyzer system which comprises a light source having a predetermined range of wavelengths, spectroscopic means including a plurality of sets of interference filters for two-wavelength photometry and adapted to be operated for producing sequentially on a time series base a plurality of light rays of different wavelengths from the light source, a first light conductor for transmitting sequentially the plurality of light rays of different wavelengths to an object under analysis, a second light conductor for sequentially receiving the plurality of modulated light rays reflected from or transmitted through the object and transmitting the modulated light rays to photoelectric converter means for converting the light rays into corresponding electric signals, means for digitizing the electric signals, and digital processing means for storing the digital signals and executing arithmetic operations on the digital signals to obtain a plurality of data corresponding to each set of the interference filters.

BRIEF DESCRIPTION OF THE DRAWINGS

The above and other objects, features and advantages of the present invention will be more apparent from description of exemplary embodiments of the invention. The description makes reference to the accompanying drawings, in which:

FIG. 12 (B) illustrates graphically and analogically a first arithmetic operation effected by an electronic computer;

FIG. 12 (C) illustrates graphically and analogically a second arithmetic operation effected by the electronic computer;

FIG. 13 illustrates graphically data signals obtained from the output of the electronic computer;

FIG. 14 shows schematically an arrangement of the spectroscopic analyzer system according to another embodiment of the invention;

DETAILED DESCRIPTION OF THE PREFERRED EMBODIMENTS

Figure 1:
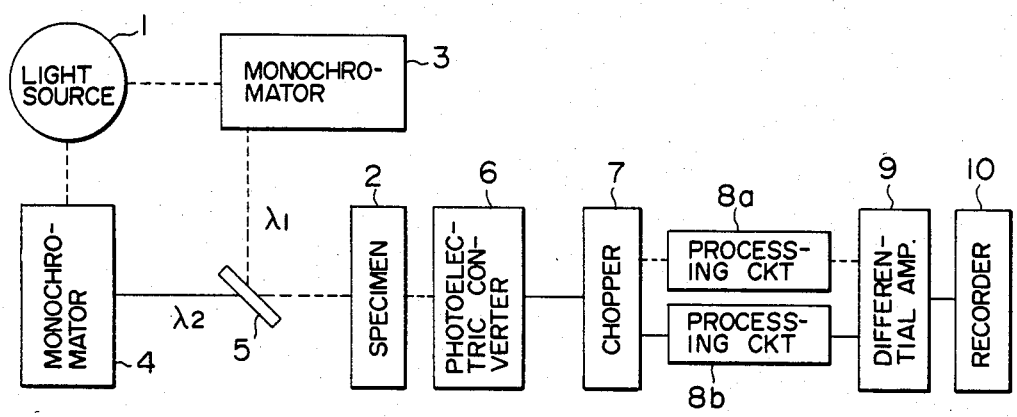
FIG. 1 shows schematically in a block diagram an arrangement of a hitherto known spectroscopic analyzer system.
Figure 2:
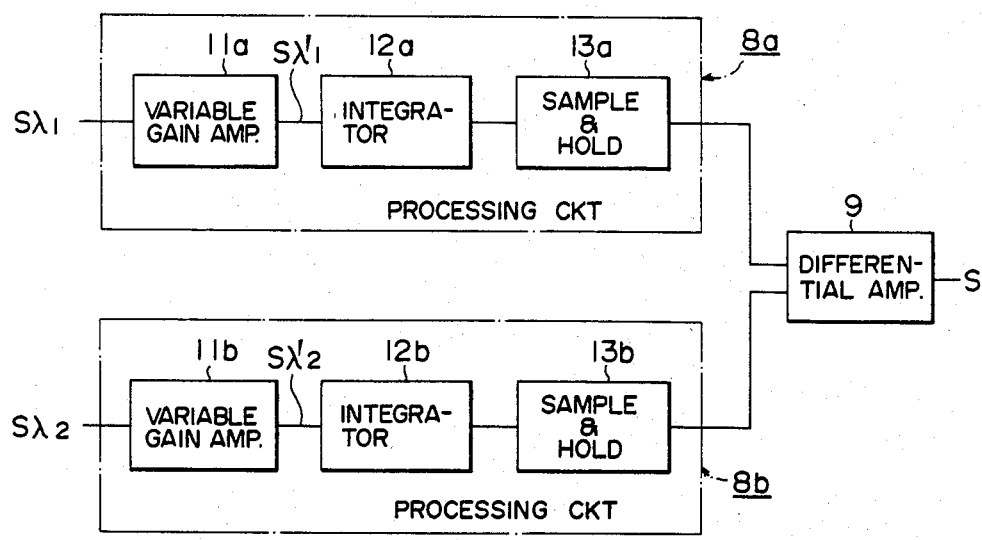
FIG. 2 shows in a block diagram a circuit configuration of signal conditioning circuits shown in FIG. 1.
Figure 3:
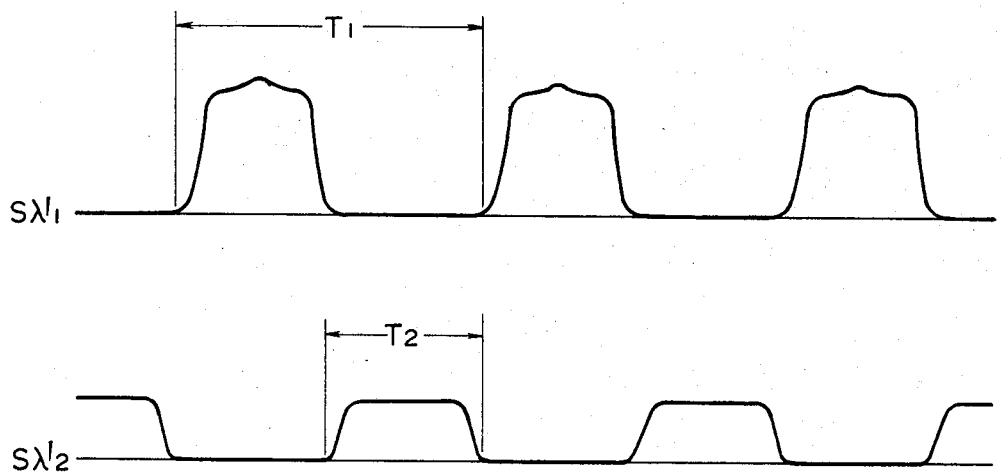
FIG. 3 illustrates graphically signals available from the outputs of the circuits shown in FIG. 2.

Now, the invention will be described in detail in conjunction with preferred embodiments thereof shown in the drawings.

Figure 4:
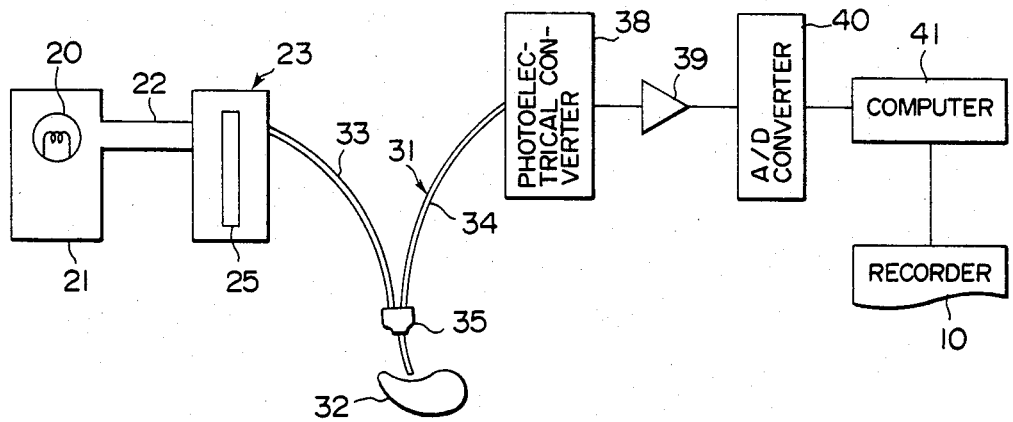
FIG. 4 shows schematically a general arrangement of a spectroscopic analyzer system according to an embodiment of the invention.

FIG. 4 shows schematically in a block diagram a general arrangement of a spectroscopical analyzer system according to an exemplary embodiment of the present invention. A reference numeral 20 designates a light source which emits light rays in a predetermined range of wavelength and may be constituted by a xenon arc lamp or the like having a wide wavelength range covering infrared to ultraviolet regions. The light source 20 is supplied with electric energy from a stabilized power supply source having a rated output, for example, of 500 W. An arc stabilizer should preferably be provided to thereby suppress variations in the light output from the lamp to a possible minimum. The light source 20 is housed in a lamp casing 21 from which a light guide 22 extends to a spectroscopic unit 23 for conducting light emitted by the light source 20 to the spectroscopic unit 23. With a view to attaining a stable transmission of light through the light guide 22, it is preferred that the inner surface of the light guide tube 22 be colored in black.

Figure 5:
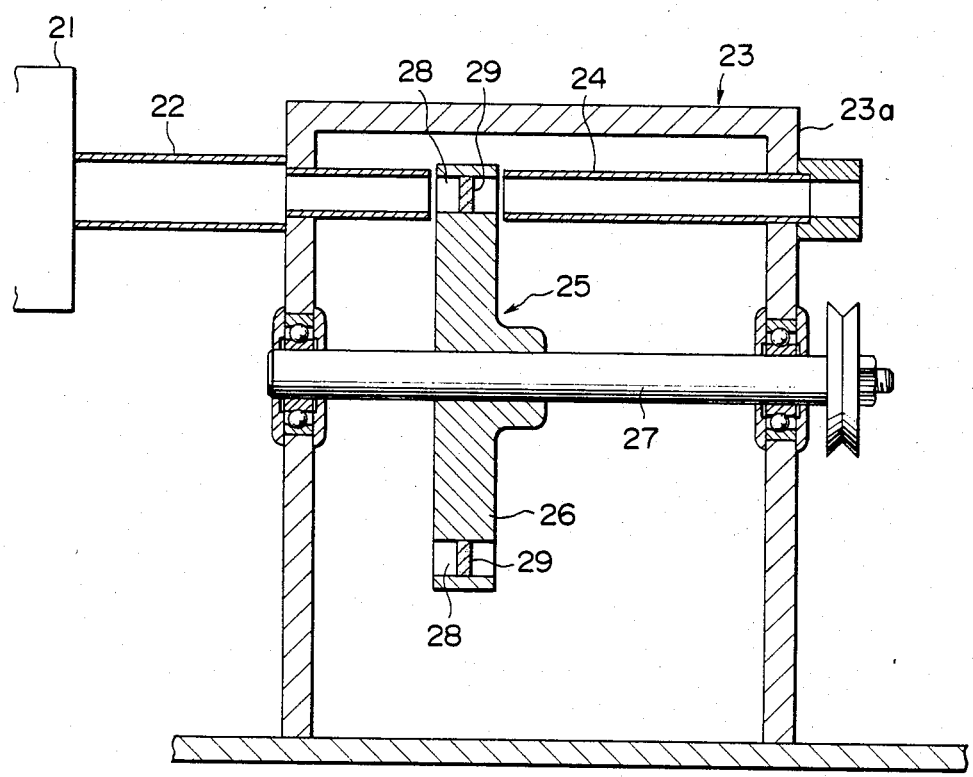
FIG. 5 shows in a partially sectional view a structure of a spectroscopic unit which can be employed according to the invention in the system shown in FIG. 2.
Figure 6:
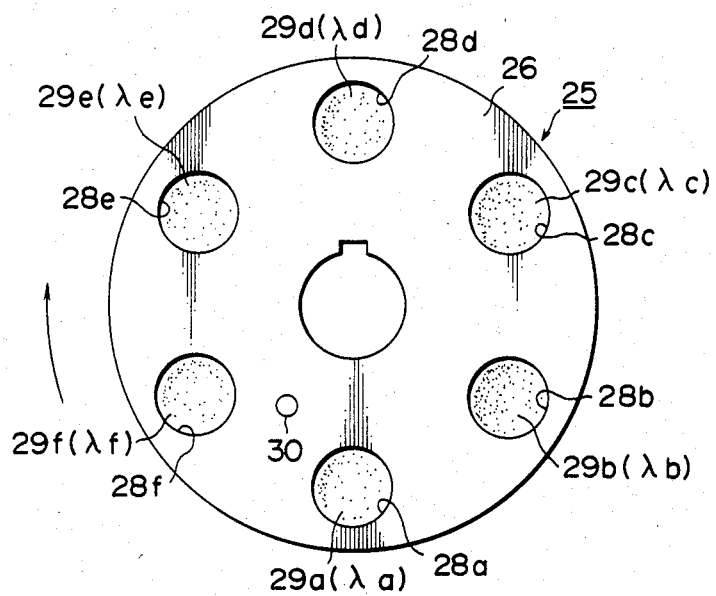
FIG. 6 shows in a front view a structure of a light chopper employed in the spectroscopic unit shown in FIG. 5.

An exemplary structure of the spectroscopic unit 23 is illustrated in detail in FIGS. 5 and 6. Referring to these figures in combination with FIG. 4, the spectroscopic unit 23 has a light-tight housing 23a in which an optical path defining tubular member 24 is stationarily disposed in axial alignment with the light guide 22. As will be seen from FIG. 5, the optical path defining tube 24 is divided into two parts so as to define a gap therebetween. The width of the gap is so selected that a rotatable light chopper 25 can pass freely through the gap to thereby interrupt the optical path 24. In more particular, the light chopper 25 is constituted by a disc 26 mounted fixedly on a shaft 27 which in turn is rotatably mounted on the housing 23a and adapted to be rotated at a high rotational frequency (e.g. 30 Hz) by a driving means (not shown). The rotatable disc 26 is provided with a plurality of transmission holes 28 formed in a peripheral portion of the disc in a circular array with a substantially same angular distance provided therebetween. When observed in the radial direction of the disc 26, the plural transmission holes 28 are positioned with a same distance from the axis of the rotatable shaft 27 so that the transmission holes 28 successively come to alignment with the optical path 24 upon rotation of the shaft 27 and hence the disc 26. Each of the transmission holes 28 is fitted with an interference filter 29 which allows monochromatic light only of a predetermine wavelength to pass therethrough. In the case of the illustrated embodiment, six transmission holes 28a, 28b, 28c, 28d, 28e and 28f are provided and fitted with the interference filters 29a, 29b, 29c, 29d, 29e and 29f, respectively, to perform two-wavelength photometry required for quantitative analysis or evaluation of pigments of oxidation and reduction types present in a vital tissue or organ to be tested. By way of example, it is assumed that the interference filters 29a and 29b serve to extract a reference wavelength $\lambda_a$ of 605 nm and a maximal absorption wavelength $\lambda_b$ of 630 nm as required for quantitatively evaluating cytochrome aa$_3$, the interference filters 29c and 29d serve to extract a reference wavelength $\lambda_c$ of 562 nm and a maximal absorption wavelength $\lambda_d$ of 575 nm required for quantitative evaluation of cytochrome b and that the interference filters 29e and 29f are to serve for extracting a reference wavelength $\lambda_e$ of 550 nm and a maximal absorption wavelength $\lambda_f$ of 540 nm required for quantitative evaluation of cytochrome c. Each of the interference filters 29a to 29f is formed of a non-metallic thin film so as to exhibit a half-value width smaller than 4 nm with a view to making the transmissivities of all the interference filters be substantially equal to one another. With the arrangement of the spectroscopic unit 28 described above, light emitted from the light source 20 and introduced through the light guide 22 to the spectroscopic unit 28 is serially extracted therefrom on a time division base as monochromatic light rays having different wavelengths $\lambda_a$ to $\lambda_f$ under the action of the light chopper 25 rotated at a high speed.

It should here be mentioned that there is provided in combination with the light chopper 25 a means for deriving a mark or reference signal at a time point immediately before the interference filter 29a, for example, intercepts the optical path 24 during the rotation of the light chopper 25, which signal is made use of as a synchronizing signal in an electronic computer 41 described hereinafter. Further, referring to FIG. 6, it will be noted that a positioning hole 30 is formed in the rotatable disc 26 to serve as a reference for establishing or determining the positional relationship among the individual interference filters 29.

Figure 7:
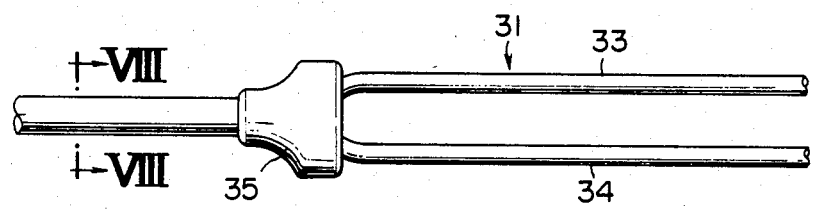
FIG. 7 shows fragmentally a configuration of a light conductor constituted by optical fibers and used in the system shown in FIG. 4.
Figure 8:
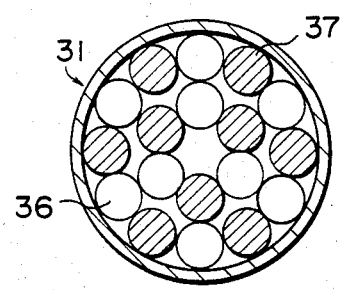
FIG. 8 is a sectional view taken along the line VIII—VIII in FIG. 7.

Referring to FIG. 7 in combination with FIG. 4, a light transmitting conductor generally denoted by a reference numeral 31 is constituted by a so-called projecting or irradiating light conductor 33 which serves to transmit the monochromatic light rays produced from the spectroscopic unit 28 mentioned above to an object 32 under test such as a living tissue or organ and a reflected light conductor 34 which serves for receiving light rays reflected from the object 32 in concern and transmitting the information carrying light rays thus obtained to a succeeding processing stage. The projecting and reflected light conductors 33 and 34 are constituted by optical fiber bundles each comprising a plurality of optical fibers 36 and 37 of quartz, respectively, as is well known in the art. Individual optical fibers 36 and 37 of the light conductors or optical fiber bundles 33 and 34 are intermingled and integrated at respective free end portions so that ends of the individual optical fibers 36 and 37 make appearance in a random array in a plane defined by an end face of the integrated end portion, as will be seen clearly in FIG. 8. In this way, the integrated or combined end portions of the irradiating and receiving light conductors 33 and 34 constitute, so to say, a probe which can be easily positioned at a desired location in the vicinity of the object 32 under test for irradiating it with the monochromatic light rays by the optical fibers 36 and receiving the reflected and modulated light rays by means of the optical fibers 37. Such positioning of the probe portion of the light conductor 31 can be easily effected due to a relatively great flexibility of the optical fiber bundles. In FIGS. 4 and 7, a reference numeral 35 denotes a clamp or the like fixture for immovably holding together the intermingled optical fibers 36 and 37 at the probe portion. By virtue of the structure of the probe portion described above, a large area can be assured for irradiating uniformly the object 32 under test and receiving effectively light rays reflected therefrom.

Figure 9:
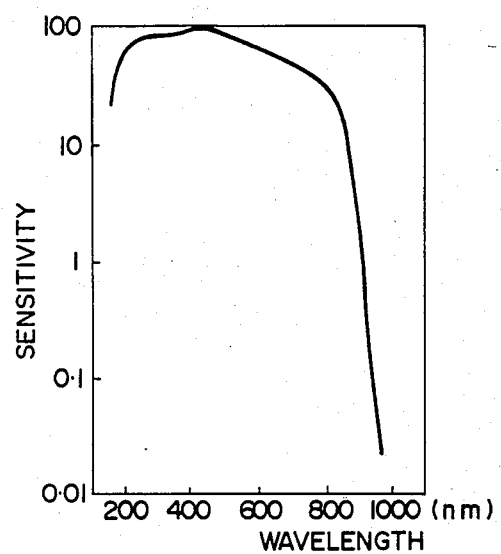
FIG. 9 graphically illustrates wavelength characteristic of a photoelectric converter element used in the system shown in FIG. 4.

The receiving light conductor or optical fiber bundle 34 is coupled to a photoelectric converter 38 which may be constituted by a photomultiplier, photo diode or the like and which serves to convert the reflected light signals inputted thereto through the optical fiber bundle 34 into corresponding electric signals. In the case of the exemplary embodiment now being elucidated, the photoelectric converter 38 is so selected that it exhibits such a sensitivity which is substantially constant over a wavelength range of 200 nm to 800 nm, as is illustrated in FIG. 9.

The electrical output signals thus derived from the photoelectric converter 38 are applied to the input of an amplifier 39 which has a linear characteristic and serves to amplify the input signals to a desired level.

The output signals from the amplifier 39 are supplied to an analog-to-digital converter (hereinafter referred to as A/D converter) 40 for converting the analog signal outputted from the amplifier 39 into corresponding digital signals at a high rate. The A/D converter 40 employed to this end may be constituted by a commercially available 16-bit A/D converter, by way of example.

The digital signals outputted from the A/D converter 39 are then supplied to an electronic computer 41 to be temporarily stored and arithmetically processed with noise being eliminated in a manner described hereinafter in detail. Data signals thus available from the output terminal of the electronic computer 41 on a desired time series base are recorded by means of a recorder 10.

For evaluating quantitatively pigments of oxidation and reduction types present in a living tissue of the object 32 under test such as an organ of a circulatory system with the aid of the spectroscopic analyzer system described above, the irradiating end face and the reflected light receiving end face of the light conductors 33 and 34 are disposed at a position close to the object 32 to be tested, while a perfusing tube 42 is connected to the object 32 in concern to thereby constitute a perfusion system 44 through which oxygen $O_2$, nitrogen $N_2$, medicines 43 and the like are supplied to the object 32. It is to be noted that an oxygen sensor 45 is disposed within the perfusing tube 42 for detecting concentration of oxygen contained in the flow within the tube 42. The output signal from the oxygen sensor 45 is supplied to the electronic computer 41 through a separately provided channel to be recorded by the recorder 10 as variations in the oxygen concentration on the time base.

Figure 11:
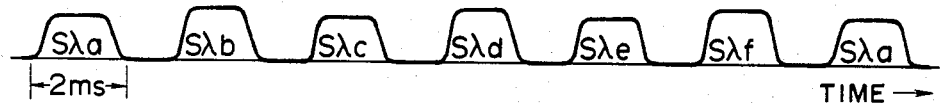
FIG. 11 graphically illustrates a waveform of signal produced from the photoelectric converter element after having being amplified.
Figure 12A:
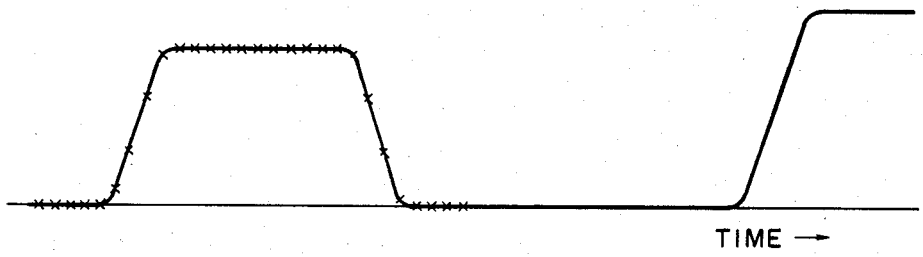
FIG. 12 (A) graphically illustrates a digitizing and sampling operation of an analog-to-digital converter.

In the state described above, light emitted by the light source 20 is introduced to the spectroscopic unit 23 through the light guide 22 and spectroscopically divided into monochromatic light rays of different wavelengths on a time division base by means of the rotating light chopper 25, as described hereinbefore, whereby monochromatic light rays of the wavelengths $\lambda_a, \ldots, \lambda_f$ are successively applied to the projecting optical fiber bundle 33 of the light conductor 31 in accordance with the positional order of the interference filters $29a, \ldots, 29f$ in the rotating direction of the light chopper 25. Thus, the object 32 in concern is successively irradiated with the monochromatic light rays of wavelengths $\lambda_a, \ldots, \lambda_f$ from the irradiating end face of the projecting optical fiber bundle 33, while the reflected light rays of the wavelengths $\lambda_a, \ldots, \lambda_f$ are successively received by the receiving end face of the optical fiber bundle 34 and transmitted to the photoelectrical converter 38 to be converted into corresponding electrical signals which are then amplified to a desired level by the amplifier 39. The waveform of the signal output from the amplifier 39 is in a form of a pulse train including pulse-like signals $S\lambda_a, \ldots, S\lambda_f$ corresponding to the monochromatic light rays extracted through the interference filters $29a, \ldots, 29f$, respectively, as is illustrated in FIG. 11 in which time is taken along the abscissa with the signal magnitude being taken along the ordinate. On the assumption that the rotational frequency of the light chopper 25 is 33 Hz, each of the pulse-like signals will have a duration of about 2 ms. The output pulse-like signals from the amplifier 39 are digitalized by the A/D converter 40 at a high rate. More specifically, the reflected light signals outputted from the amplifier 39 is sampled by the A/D converter 40 in accordance with a program stored in the electronic computer 41 at a sampling rate of the order of micro seconds ($\mu$S) as indicated by the sampling time points marked X in FIG. 12(A).

The sampled signals thus produced are stored in a memory incorporated in the electronic computer 41. In this connection, it should be noted that the correspondence between the pulse-like signals $S\lambda_a, \ldots, S\lambda_f$ and the relevant interference filters $29a, \ldots, 29f$ can be identified by the reference signal produced by a suitable means (not shown) of the spectroscopic unit 23, as described hereinbefore.

Figure 12B:
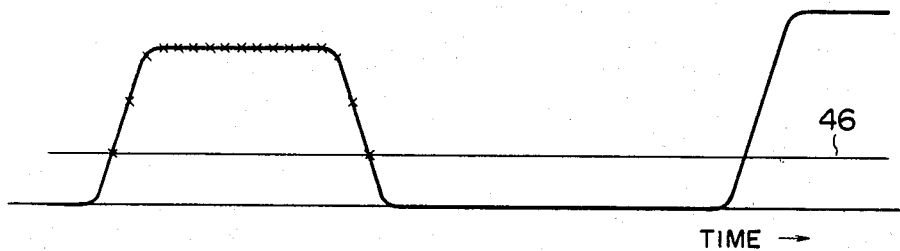

Subsequently, two types of processings are performed on the sampled digital signal stored in the memory. In the first processing, the sampled digital signals are subjected to comparison with a reference level 46 (e.g. 0.5 volts), as schematically illustrated in FIG. 12(B), wherein only the sampled signals of magnitudes higher than the reference level 46 are determined to be utilized as data quantity representing the reflected light signal $S\lambda_i$ (wherein i is a, b, c, d, e or f), provided that five sampled digital signals exceeding the level 46 make appearance in succession, by way of example. Through this processing, the so-called white noise can be eliminated, to an advantage.

Figure 12C:
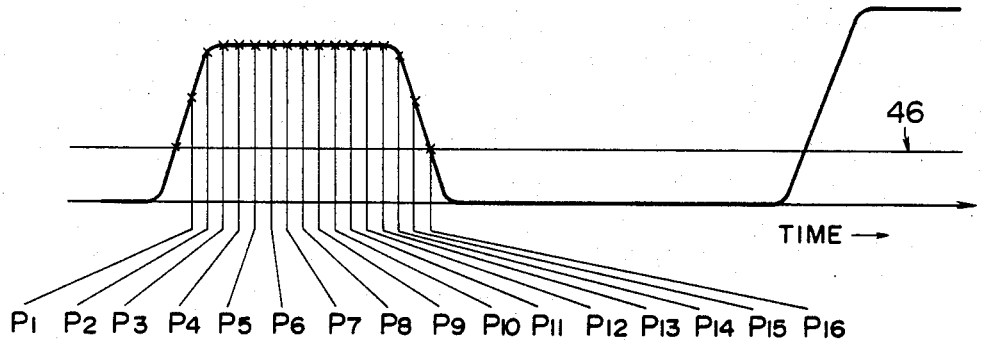

In the second phase of processing, more accurate data value is derived from the data quantity obtained through the first processing. In more particular, assuming that 16 digital signals are sampled validly from the single reflected light signals $S\lambda_i$ as indicated by $P_1, P_2, \ldots, P_{16}$ in FIG. 12(C), the sampling time points $P_1, P_2$ and $P_3$ as well as $P_{14}, P_{15}$ and $P_{16}$ occur during the rise-up period and the falling period of the reflected light signal $S\lambda_i$, respectively. Accordingly, the sampled digital signals corresponding to these sampling time points are neglected, and only the digital signals sampled at the remaining sampling time points, that is $P_4, \ldots, P_{13}$ in the case of the illustrated embodiment, are considered as valid data which are subsequently subjected to arithmetic operation to determine the arithmetic mean or geometric mean. Through this second processing, the white noise can be further eliminated.

The arithmetic processings of the sampled digital signals derived from each of the reflected light signals $S\lambda_a, \ldots, S\lambda_f$ are performed repeatedly, for example, for 50 reflected light signals $S\lambda_i$ derived from the same interference filter, to thereby obtain the mean data $S_A$ to $S_F$ for each of the reflected light signals $S\lambda_a, \ldots, S\lambda_f$ at a rate of 0.5 to 1 second.

On the basis of the mean data $S_A, \ldots, S_F$ obtained for the reflected light signals $S\lambda_a, \ldots, S\lambda_f$, respectively, logarithmic differences between data $S_B$ and $S_A$, $S_D$ and $S_C$ and $S_F$ and $S_E$ are arithmetically determined, resulting in that output signals $S_B-S_A$, $S_D-S_C$ and $S_F-S_E$ are produced at a given rate of 0.5 sec. to 1 sec. and supplied through appropriate interface to the recorder 10 to be recorded on a recording sheet, as is illustrated in FIG. 13. In case the object 32 under test is not stationary but movable, the distance between the object 32 and the probe end portion of the light conductor 31 and hence the effective length of the whole optical path may undergo variations, involving noise or drift in the data signals. However, such noise or drift can be readily cancelled out or compensated through appropriate processing executed by the electronic computer. For example, it will be readily possible to measure variation in the length of the optical path from time to time by determining variation in the quantity of light of a reference wavelength transmitted along the optical path, wherein the optical path length is correspondingly corrected in the sense to cancel out the noise or drift.

Figure 10:
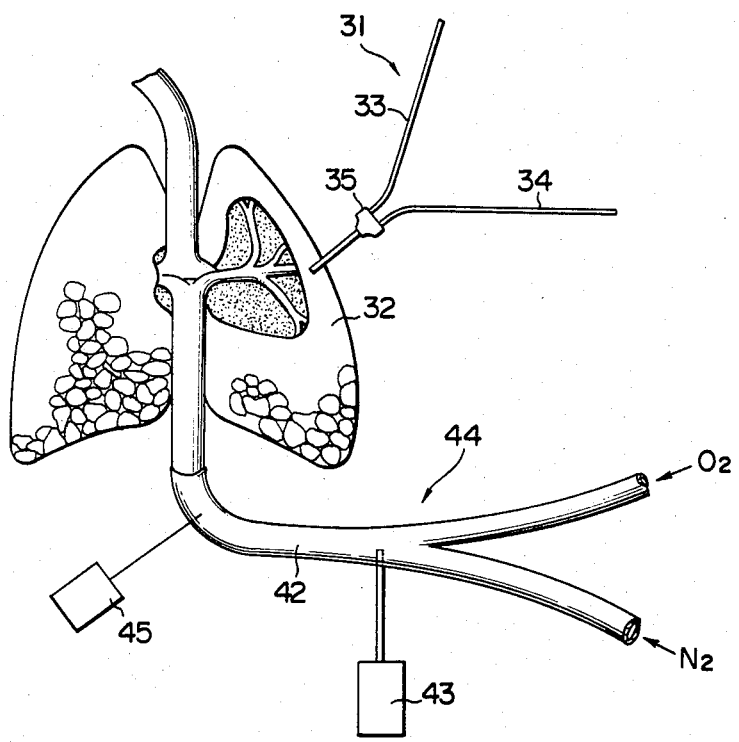
FIG. 10 illustrates a perfusing system in the state in which an object is being spectroscopically tested.

The data signals $S_B-S_A$, $S_D-S_C$ and $S_F-S_E$ finally obtained are graphically illustrated by curves I, II and III, respectively, in FIG. 13, wherein the curve I, II and III represent, respectively, changes occurred in cytochromes aa$_3$, b and d as the result of oxidation or reduction. It will be seen from these graphs that all of cytochromes undergo changes of reduction type upon injection of $N_2$ in the perfusing tube 42 (FIG. 10). Above all, change of cytochrome aa$_3$ is remarkable. Further, upon injection of thianide KCN in the perfusing tube 42, cytochromes exhibit significant changes ascribable to reduction, among which change of cytochrom b is most remarkable. These changes of pigments of oxidation and/or reduction type present in living organs on a time series base are representative of medicinal metabolism in a circulatory system and provided very meaningful biogenic information. Most of noises observed in the curves shown in FIG. 13 are believed to be ascribable to pulsation brought about by a perfusing pump (not shown) used in the perfusing system 44.

Figure 15:
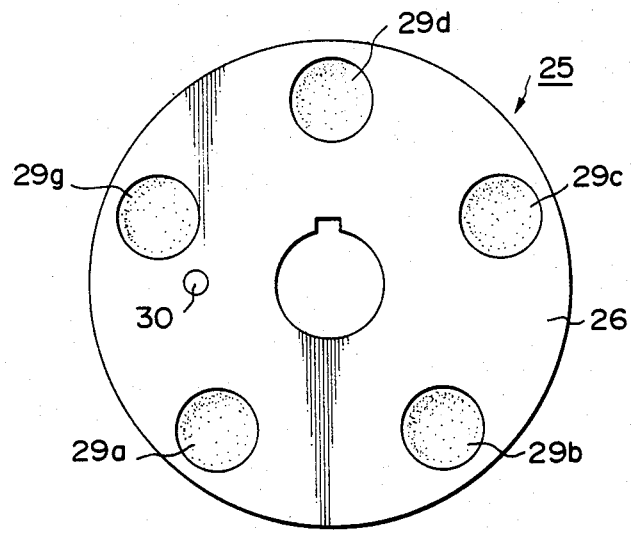
FIG. 15 shows in a front view a structure of a light chopper used in the system shown in FIG. 14.

FIGS. 14 and 15 show a spectroscopic analizer system according to another exemplary embodiment of the invention.

The spectroscopic analyzer system shown in FIGS. 14 and 15 is different from the system described above in that the rotatable light chopper 25 includes an interference filter 29g (having a transmitting wavelength of 340 nm) for producing fluorescence in addition to the interference filters 29a; 29b and 29c; 29d required for quantitatively evaluating cytochrome aa$_3$ and cytochrome b. Further, the reflected light conductor 34 is bifurcated at 48, wherein one of the branched light conductor 34a is coupled directly to the photoelectric converter 38 so that the corresponding electric signal resulted from the photoelectric conversion is supplied to the A/D converter 40 through the amplifier 39, while the other branched light conductor 34b is coupled to another photoelectric converter 38' through a fluorescence selecting interference filter 47 having a transmitting wavelength of 450 nm, the output signal from the converter 38' being supplied to the A/D converter 40 by way of a different channel including an amplifier 39'. The reference numeral 48 indicates a clamp or fixture for securing the bifurcated portion.

With the arrangement of the spectroscopic analyzer system shown in FIGS. 14 and 15, data representative of oxidation and/or reduction of cytochrome aa$_3$ and cytochrome b are obtained through the same processing as described hereinbefore. Additionally, fluorescence reflected or excited by the object 32 under test in response to the irradiating light ray passed through the interference filter 29g for fluorescence emission is detected by the photoelectric converter 38' through the fluorescence selecting interference filter 47. The output signal from the photoelectric converter 38' is stored in the electronic computer 41 after having been digitalized and subsequently undergoes arithmetic operation to be outputted as fluorescence data on a time series base with noise being concurrently eliminated.

Such fluorescence is attributable to cytoplasmic pyridine-nucleoside. In FIG. 13, a curve IV represents fluorescence data as obtained by injecting ethyl alcohol (EtOH) in the perfusing tube 42. It will be seen that cytoplasmic pyridine-nucleoside exhibits reduction type reaction with ethyl alcohol.

Figure 16:
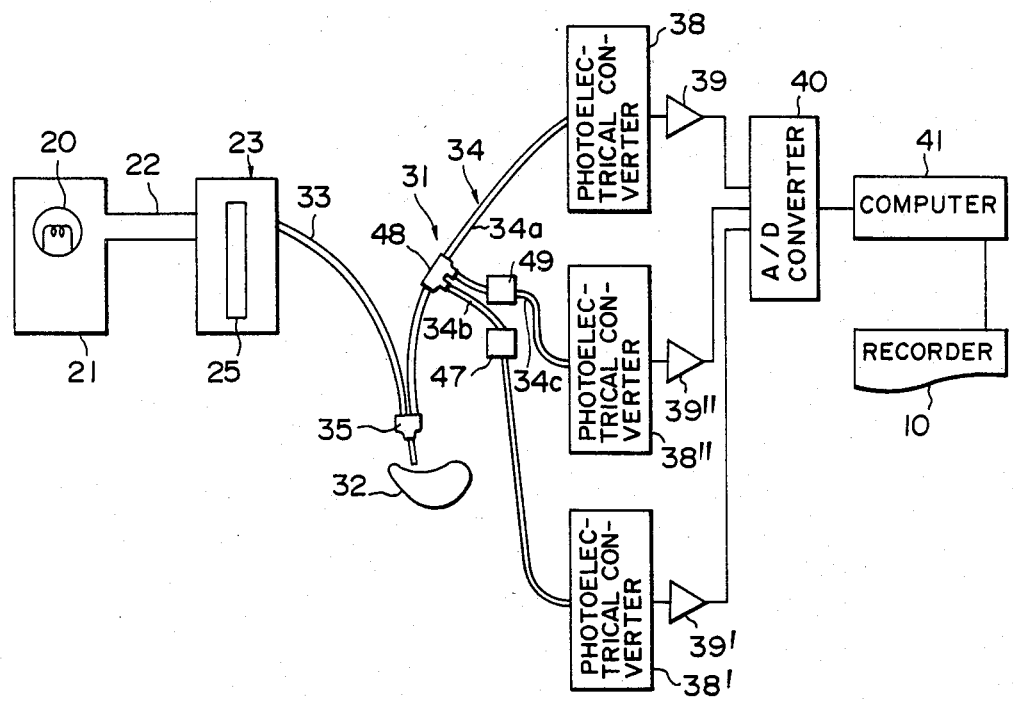
FIG. 16 shows a modification of the spectroscopic analyzer system shown in FIG. 14.

Although it has been described that the fluorescence selecting filter 47 is disposed at the branched reflected light conductor 34b. However, this filter 47 may equally be installed in the rotatable chopper 25 to a simplification of the system. Further, in consideration of the fact that reflecting of the very fluorescence excitation light ray having wavelength of 340 nm gives rise to variation in emitted fluorescence, the branched reflected light conductor 34b may be again bifurcated, wherein a sub-branched reflected light conductor 34c is coupled to another photoelectric converter element 38'' through an interposed interference filter 49 having a transmitting wavelength of 340 nm, as is shown in FIG. 16. The output signal from the photoelectric converter 38'' is supplied to the A/D converter 40 through an amplifier 39'', wherein the signal component corresponding to the reflected light signal taken out through the sub-branched light conductor 34c is subtracted from the fluorescence signal derived from the light signal supplied through the light conductor 34b through corresponding arithmetic operation. Then, more accurate measurement of fluorescence can be assured. As the alternative, the fluorescence signal and the reflected light signal outputted from the photoelectric converter elements 38' and 38'', respectively, may be supplied to a substractor (not shown) to thereby detect difference between these signals 38' and 38'', wherein the difference signal thus derived is arithmetically processed by the electric computer 41 after analog-to-digital conversion through the A/D converter 40, to thereby compensate variation of the received fluorescence signal brought about by the fluorescence exciting light ray per se.

Figure 17:
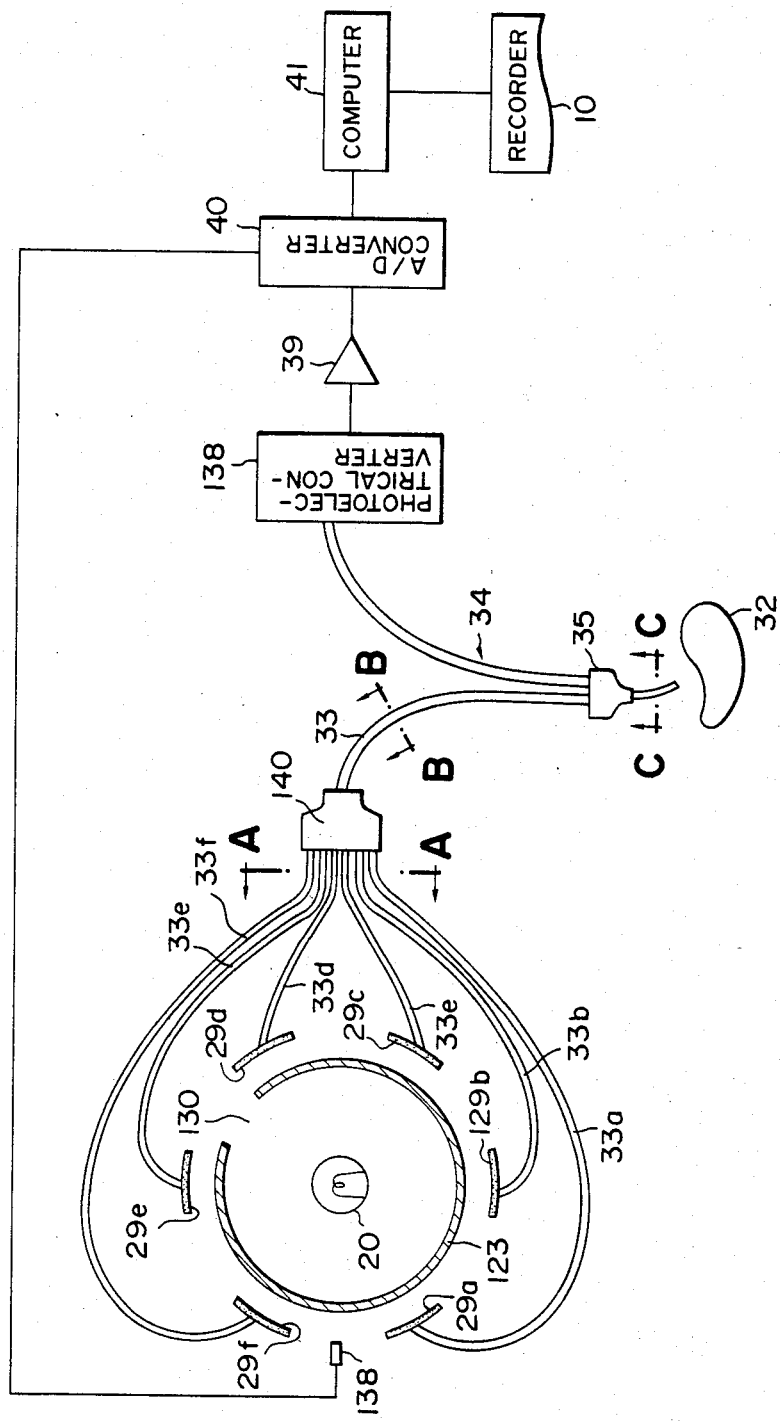
FIG. 17 shows schematically a general arrangement of a spectroscopic analyzer system according to still another embodiment of the invention.
Figure 18:
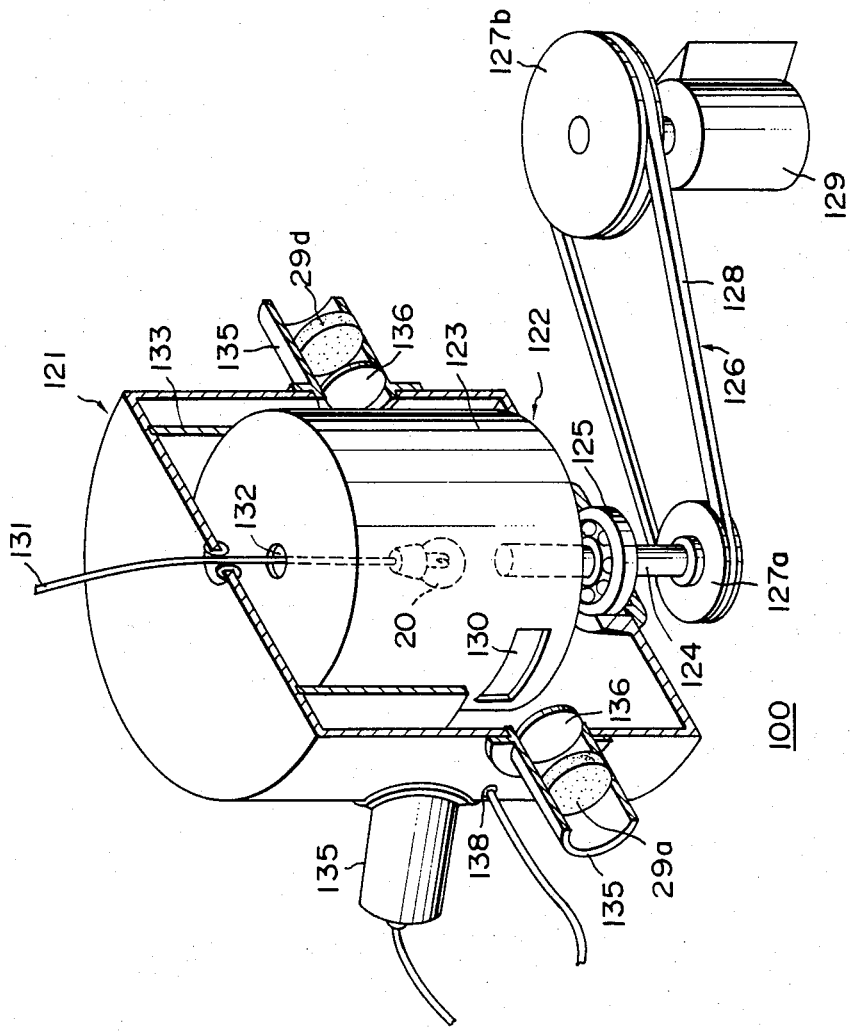
FIG. 18 shows in a perspective view a structure of a spectroscopic unit used in the system shown in FIG. 17.
Figure 19A:
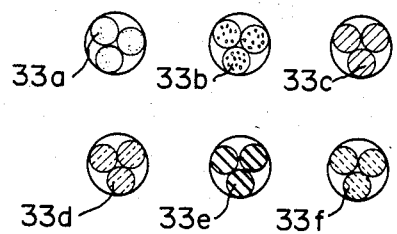
FIGS. 19 (A), (B) and (C) show cross-sections of optical fiber bundles taken along the lines A—A, B—B and C—C in FIG. 17.
Figure 19B:
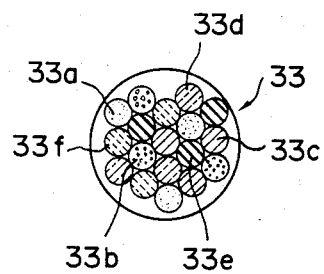
Figure 19C:
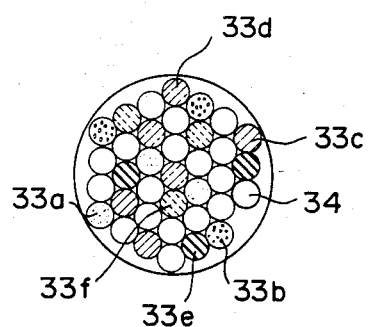

In FIGS. 17 to 19, there is shown a spectroscopic analyzer system according to still another embodiment of the present invention. In these figures, components similar or equivalent to those shown in FIG. 4 are denoted by same reference numerals.

Referring at first to FIGS. 17 and 18, a light source which may be constituted by an xenon arc lamps having a wide range of wavelength covering infrared and ultraviolet regions is disposed within a cylindrical housing 121 having closed top and bottom at a substantially center position. The light source 20 is supplied with a stabilized power source (not shown) having a rated output of 500 W. Further, an arc stabilizer (not shown) may be provided so as to suppress variation in the light output to a possible minimum.

In a spectroscopic unit generally denoted by a reference numeral 100, there is disposed within the cylindrical housing 121 a rotor 122 which is adapted to be rotated at a high speed and constituted by a cylindrical slit member 123 having closed top and bottom and encasing therein the light source 20. The bottom wall of the cylindrical slit member 123 is fixedly mounted on a shaft 124 at the center, which shaft 124 extends downwardly and is rotatably supported by a ball bearing 125 which in turn is fixedly mounted on the bottom wall of the cylindrical housing 121. It will be seen that the shaft 124 is adapted to be driven by a motor 129 through a transmission 126 constituted by pulleys 127a and 127b and a belt 128. Thus, the cylindrical slit member 123 can be rotated at a high speed (e.g. 33 Hz) about the axis of the shaft 124. A slit 130 is formed in the peripheral wall of the cylindrical rotor 122 at a lower end portion thereof. A conductor 131 for connecting the light source 20 to the power supply source is led out through an opening 32 formed in the top wall of the cylindrical slit member 23 and a hole formed in the top wall of the housing 121 in a light-tight manner to be connected to the power supply source. Further, a cylindrical shield member 133 depends downwardly from the top wall of the housing 121 and encloses an upper half of the cylindrical slit member 123. This shield member 133 serves to prevent light leakage possibly occurring through the opening 132 from affecting adversely light scanning operation effected by the slit 130.

Mounted fixedly on the peripheral wall of the stationary cylindrical housing 121 along and in opposition to a circular path followed by the slit 130 upon rotation of the cylindrical slit member 123 are a plurality of wave guides 135 with an equal angular distance therebetween so that the wave guides 135 successively come to axial alignment with the light source 20 through the slit 130 upon rotation of the cylindrical slit member 123. In the case of the illustrative embodiment being described, six wave guides 135 are provided, wherein each of the wave guides 135 is fixedly fitted with a condenser lens 136 so as to be scanned once by the light beam through the slit 130 for each rotation of the cylindrical slit member 123. Further, the wave guides 135 are provided with interference filters 29a, ..., 29f on the outer side of the condenser lenses 136, respectively, to perform two-wavelength photometry required for quantitative analysis or evaluation of pigments of oxidation and reduction types present in living tissue or organs to be tested. By way of example, it is assumed that the interference filters 29a and 29b serve to extract a reference wavelength $\lambda_a$ of 605 nm and a maximal absorption wavelength $\lambda_b$ of 630 nm required for quantitative analysis of cytochrome aa$_3$, the interference filters 29c and 29d are to serve for extracting a reference wavelength $\lambda_c$ of 562 nm and a maximal absorption wavelength $\lambda_d$ of 575 nm suited for quantitative evaluation of cytochrome b and that the interference filters 29e and 29f are to serve for extracting a reference wavelength $\lambda_e$ of 550 nm and a maximal absorption wavelength $\lambda_f$ of 540 nm suited for quantitative identification of cytochrome c. Each of the interference filters 29a to 29f is formed of a non-metallic thin film so as to exhibit a half-value width smaller than 4 nm with a view to making the transmittivities of all the interference filters be substantially equal to one another. Further, a hole 138 is formed in the cylindrical side wall of the housing 121 at a position between the light guides 135 in which the interference filters 29a and 29f are fitted, respectively so as to be scanned by light beam through the slit 130. A photoelectric sensor or the like may be placed in the hole 135 to produce an electric signal which is utilized in the electric processing as the synchronizing or marker signal in the manner described hereinbefore in conjunction with the exemplary embodiment shown in FIGS. 4 to 12.

As is schematically illustrated in FIG. 17, optical fiber bundles 33a, ..., 33f are optically coupled to the interference filters 29a to 29f, respectively. Each of the optical fiber bundles 33a, ..., 33f is constituted by a number of optical fibers of quartz-based material, as is clearly shown in FIG. 19 (A). These optical fiber bundles 33a, ..., 33f are combined together and integrated to a single optical fiber bundle which corresponds to the irradiating or projecting light conductor mentioned hereinbefore in conjunction with the system shown in FIG. 4 and is thus designated by the same reference numeral 33. In this connection, it is important to note that the optical fiber bundles 33a, ..., 33f are so combined that the individual optical fibers are randomely intermingled in a manner illustrated in FIG. 19(B) in a cross-sectional view. A reference numeral 140 denotes a clamp or fixture for holding rigidly the intermingled or combined optical fiber bundles. On the other hand, the free end portion of the irradiating or projecting light conductor 33 is integrated with one end portion of the reflected light conductor 34 in such a manner that ends of the individual optical fibers of the light conductors 33 and 34 make appearance in a random array in a plane defined by an end face of the integrated end portion, as will be clearly seen in FIG. 19 (C). In this way, the integrated or combined end portions of the irradiating and receiving light conductors 33 and 34 constitute, so to say, a probe which can be easily positioned at a desired location in the vicinity of the object 32 under test for irradiating it with the monochromatic light rays by the light conductor 33 and receiving the reflected and modulated light rays by means of the reflected light receiving and transmitting conductor 37. A reference numeral 35 denotes a clamp or the like fixture for immovably holding together the intermingled optical fibers 33 and 34. By virtue of the structure of the probe portion described above, a large area can be assured for irradiating uniformly the object 32 under test and receiving effectively light rays reflected therefrom. The receiving light conductor 34 is coupled to a photoelectric converter 38 which serves for the same function as that of the photoelectric converter described hereinbefore in conjunction with the system shown in FIG. 4 and others. The electronic signal processing stages inclusive of the A/D converter and others which are provided in succession to the photoelectric converter 38 are of same configurations and functions as those described hereinbefore. Accordingly, further elucidation of them will be unnecessary.

Operation of the spectroscopic unit shown in FIGS. 17 and 18 will be self-explanatory. As the cylindrical slit member 123 is rotated at a high speed, the interference filters 29a, ..., 29f are successively scanned by light ray from the light source 20 through the rotating slit 130, whereby monochromatic light rays $\lambda_a, ..., \lambda_f$ are successively produced and transmitted through the optical fiber bundles 33a to 33f to irradiate the object 32 under test, whereby the resulting monochromatic rays reflected from the object 32 are transmitted through the receiving light conductor 34 to the photoelectric converter 38. The processing of the electric signals outputted from the converter 38 to obtain the desired data is effected in the same manner as in the case of the preceding exemplary embodiments. Further, it goes without saying that various modifications or additions made as to the embodiment shown in FIG. 4 applies valid to the system shown in FIGS. 17 et seq. Accordingly, repeated description is omitted.

In all the exemplary embodiments described in the foregoing, it has been assumed that the xenon arc lamp is employed as the light source 20. However, the invention is never restricted to the use of the xenon lamp. Since it is sufficient for the light source 20 to emit the light rays in a visible range, other lamps such as tungsten filament lamp and the like can be employed. Further, the interference filters are also never restricted to those for quantitatively evaluating cytochromes and for producing fluorescence. Other types of interference filters can of course be employed in the spectroscopic analyzer systems according to the invention. For example, interference filters for deriving light rays having a reference wavelength of 456 nm and maximal absorption wavelength of 500 nm, respectively, can be used for quantitatively identifying flavin adenine dinucleotide, while interference filters for producing light rays having a reference wavelength of 675 nm and a maximal absorption wavelength of 685 nm may be used for determining concentration of calcium contained in cells. In the foregoing, description has been made on the assumption that light information obtained from light rays reflected by the object under test is utilized for the aimed quantitative evaluation or identification. However, it is equally possible to make use of the light information derived from the light rays transmitted through the object under test in the electronic signal processing described hereinbefore. Further, other parameters such as moisture and temperature can be monitored by the electronic computer 41 in additions to concentration of oxygen. Finally, it should be mentioned that the spectroscopic analyzer systems according to the invention can be used for other applications such as spectroscopical analyses of living tissues and organs of plants and animals as well as environmental and industrial applications. As will be appreciated from the foregoing description, the spectroscopical analyzer system according to the invention makes it possible to evaluate pigments of reduction and oxidation types present in living tissues, cells or organ in a straightforward manner on the basis of light information obtained from living objects under test without necessity of previously preparing specimens and, besides, allows such evaluation to be performed on a plurality of pigments in concern simultaneously on a time series base with an enhanced efficiency and accuracy. Accordingly, not only biological informations which are very important for determining influences of medicines, variations in oxygen concentration, ischemia, metabolism of hormone and the like in circulatory systems and others can be obtained for intravital tissues or cells of animals and plants of wide varieties, but also informations useful for environmental control and/or industrial purposes are available with an improved reliability with disturbing noises being suppressed to a minimum. Further, the time required for the analyses can be reduced significantly.

Although the invention has been described in conjunction with the preferred embodiments it will be appreciated that the invention is never restricted to them but various modifications and variations as well as changes in design may readily occur to those skilled in the art without departing from the spirit and scope of the invention set forth in claims.

I claim:

1. A spectroscopic analyzer system for examining intravital tissues, comprising:

a light source having a predetermined range of wavelength;

spectroscopic means including a plurality of sets of interference filters for two-wavelength photometry and adapted to be operated for producing sequentially on a time series base a plurality of light rays of different wavelengths from said light source;

a first light conductor from transmitting sequentially the plurality of light rays of different wavelengths to an object under analysis;

a second light conductor for sequentially receiving the plurality of modulated light rays reflected from or transmitted through said object and transmitting the modulated light rays to photoelectric converter means for converting the light rays into corresponding electric signals;

means for digitizing said electric signals; and digital processing means for storing said digital signals and executing arithmetic operation on the digital signals in a manner that noises are eliminated to obtain a plurality of time series data corresponding to each set of the interference filters;

said spectroscopic means comprising a light chopper constituted by a rotatable disc adapted to be rotated at a predetermined speed by a driving means, and said plurality of the interference filters are, respectively, mounted in a plurality of through-holes formed in said rotatable disc in a peripheral portion thereof in a circular array with adjacent ones of said interference filters being spaced by a substantially same distance from one another, said rotatable disc being so positioned relative to an optical path of light emitted by said light source that said optical path is intermittently and successively intercepted by said interference filters, and said first light conductor has an inlet end disposed in succession to said light chopper so as to receive light rays produced by said interference filters successively on a time division base, said first light conductor being constituted by a bundle of optical fibers;

an interference filter for fluorescence excitation is additionally provided in said disc in circular alignment with said interference filters for the two-wavelengths photometry;

a third light conductor is branched from said second light conductor and optically coupled to second photoelectric converter means by way of an interposed fluorescence selecting filter, said means being connected to said digitizing means;

a fourth light conductor is branched from said second light conductor and optically coupled to a third photoelectric converter means by way of an interposed fluorescence selecting filter, said photoelectric converter means being connected to said digitizing means.

2. A spectroscopic analyzer system for examining intravital tissues, comprising:

a light source having a predetermined range of wavelength;

spectroscopic means including a plurality of sets of interference filters for two-wavelength photometry and adapted to be operated for producing sequentially on a time series base a plurality of light rays of different wavelengths from said light source;

a first light conductor for transmitting sequentially the plurality of light rays of different wavelengths to an object under analysis;

a second light conductor for sequentially receiving the plurality of modulated light rays reflected from or transmitted through said object and transmitting the modulated light rays to photoelectric converter means for converting the light rays into corresponding electric signals;

means for digitizing said electric signals;

digital processing means for storing said digital signals and executing arithmetic operation on the digital signals in a manner that noises are eliminated to obtain a plurality of time series data corresponding to each set of the interference filters;

said spectroscopic means comprising a cylindrical slit member mounted rotatably around said light source and having a peripheral wall formed with a slit, and a cylindrical stationary housing disposed so as to enclose therein said rotatable cylindrical slit member, wherein said plurality of the interference filters are fixedly disposed in a peripheral wall of said stationary cylindrical member in a circular array so as to be scanned successively with light emitted from said light source through said slit upon rotation of said cylindrical slit member, said interference filters being spaced by a substantially same distance from one another, and wherein said interference filters being optically coupled to inlet ports of optical fiber bundles, respectively, said optical fiber bundles having outlet end portions randomly integrated together into said first conductor.

3. A spectroscopic analyzer system for examining intravital tissues according to claim 2, wherein:

said second light conductor being constituted by a bundle of optical fibers, said optical fibers of said first and second light conductors are intermingly combined together at respective outlet and inlet end portions to thereby constitute a probe portion adapted to be located at a selected position close to said object under analysis and having a flat end in a plane in which ends of said optical fibers being randomly arrayed, said second light conductor having an outlet end optically coupled to photoelectric converter means.

4. A spectroscopic analyzer system for examining intravital tissues according to claim 2 wherein:
an interference filter for fluorescence excitation is additionally provided in said stationary cylindrical housing in circular alignment with said interference filters for the two-wavelength photometry.

5. A spectroscopic analyzer system for examining intravital tissues according to claim 2 wherein:
a third light conductor is branched from said second light conductor and optically coupled to second photoelectric converter means by way of an interposed fluorescence selecting filter and means being connected to said digitizing means.

6. A spectroscopic analyzer system for examining intravital tissues according to claim 2 wherein:
a reference signal generating means is provided in said stationary cylindrical housing for producing a reference signal to be utilized in operation of said digitizing means and said digital processing means for synchronization of correspondence between said interference filters and said electric signals.

7. A spectroscopic analyzer system for examining intravital tissues according to claim 5 wherein:
a fourth light conductor is branched from said second light conductor and optically coupled to a third photoelectric convertor means by way of a interposed fluorescence selecting filter, said third photoelectric converter means being connected to said digitizing means.

8. A spectroscopic analyzer system for examining intravital tissues according to claim 4 wherein:
a third light conductor is branched from said second light conductor and optically coupled to second photoelectric converter means by way of an interposed fluorescence selecting filter, said means being connected to said digitizing means; and
a fourth light conductor is branched from said second light conductor and optically coupled to a third photoelectric converter means by way of an interposed fluorescence selecting filter, said third photoelectric converter means being connected to said digitizing means.

* * * * *